(12) United States Patent
Ebrahim et al.

(10) Patent No.: US 9,885,728 B2
(45) Date of Patent: Feb. 6, 2018

(54) VALUE ASSIGNMENT FOR CUSTOMIZABLE QUALITY CONTROLS

(71) Applicant: Bio-Rad Laboratories, Inc., Hercules, CA (US)

(72) Inventors: Alireza Ebrahim, Laguna Niguel, CA (US); Karl De Vore, Coto De Caza, CA (US); Christopher Spates, Laguna Hills, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 99 days.

(21) Appl. No.: 14/831,765

(22) Filed: Aug. 20, 2015

(65) Prior Publication Data

US 2016/0054339 A1 Feb. 25, 2016

Related U.S. Application Data

(60) Provisional application No. 62/041,398, filed on Aug. 25, 2014.

(51) Int. Cl.
| | | |
|---|---|---|
| *G01N 33/96* | (2006.01) | |
| *G01N 33/78* | (2006.01) | |
| *G01N 33/48* | (2006.01) | |

(52) U.S. Cl.
CPC .......... *G01N 33/78* (2013.01); *G01N 33/96* (2013.01); *G01N 33/48* (2013.01)

(58) Field of Classification Search
CPC ........ G01N 33/48; G01N 33/96; G01N 33/78; Y10T 436/25
USPC .......... 436/8, 19, 55, 174; 435/4; 252/408.1; 702/85, 104
See application file for complete search history.

(56) References Cited

U.S. PATENT DOCUMENTS

| | | | | |
|---|---|---|---|---|
| 5,257,212 A | * | 10/1993 | Kildal-Brandt | ...... G01N 21/274 702/25 |
| 6,251,684 B1 | * | 6/2001 | Buhl | ............... A61K 9/1694 210/198.2 |
| 9,354,144 B2 | * | 5/2016 | Ebrahim | ............... G01N 33/96 |
| 9,599,543 B2 | * | 3/2017 | Ebrahim | ............... G01N 33/96 |
| 2006/0068399 A1 | | 3/2006 | McMillan et al. | |
| 2014/0329263 A1 | * | 11/2014 | Ebrahim | ............... G01N 33/96 435/22 |
| 2016/0084861 A1 | * | 3/2016 | Kleider | ............... G01N 33/50 436/501 |

FOREIGN PATENT DOCUMENTS

WO      2013043388 A1      3/2013

OTHER PUBLICATIONS

Anonymous: "Guidelines for quality management in soil and plant laboratories", Quality of Analytical Procedures, Chapter 7, Retrieved from the Internet: URL:http:l/web.archive.org/web/20130724030703/http://www.fao.org/docrep/w7295e/w7295e09.htm, Jul. 24, 2013, 27 pages.

EP15180886.2 , "Extended European Search Report", dated Feb. 18, 2016, 10 pages.

* cited by examiner

*Primary Examiner* — Maureen Wallenhorst
(74) *Attorney, Agent, or Firm* — Kilpatrick Townsend & Stockton LLP

(57) ABSTRACT

Methods are provided for end users of diagnostic measurement procedures to prepare quality controls having desired analyte recoveries, estimate recoveries of quality controls already prepared, and compare estimated and measured recoveries. To prepare a quality control containing a particular analyte, a desired recovery of a measurement procedure for the analyte can be scaled by a correlation factor to obtain a target nominal concentration of the analyte in the quality control. Alternatively, the nominal concentration of an analyte in a quality control can be scaled by a correlation factor to obtain a predicted recovery of a measurement procedure for the analyte. The correlation factors can be based on recovery data previously obtained using the measurement procedure and optionally one or more reference procedures, and can be calculated using regression analysis of these data. Each quality control can be prepared by dissolving a number of solid beads containing the analyte(s) of interest in a volume of base matrix.

12 Claims, 9 Drawing Sheets

FIG. 4
(prior art)

| T4 Analyte Control Bead Reconstitution Spreadsheet | | | |
|---|---|---|---|
| User input | | | |
| Bead Number | | 2 | |
| Reconstitution Volume (mL) | | 5 | |
| | | Expected Recovery | |
| Test Method | | µg/dL | nM |
| Abbott Architect | | 10.9 | 140.4 |
| Alfa Wasserman ACE | | 10.4 | 134.2 |
| Beckman Coulter Unicel | | 10.3 | 133.2 |
| Biomerieux Vidas | | 9.6 | 124.1 |
| Ortho Vitros | | 9.9 | 127.1 |
| Roche Elecsys | | 10.0 | 128.4 |
| Siemens Advia Centaur | | 11.4 | 147.4 |

*FIG. 7*

| T4 Analyte Control Bead Reconstitution Spreadsheet | | | |
|---|---|---|---|
| User input | | | |
| Bead Number | | 2 | |
| Reconstitution Volume (mL) | | 10 | |
| | | Expected Recovery | |
| Test Method | | µg/dL | nM |
| Abbott Architect | | 5.44 | 70.2 |
| Alfa Wasserman ACE | | 5.30 | 68.4 |
| Beckman Coulter Unicel | | 5.28 | 68.0 |
| Biomerieux Vidas | | 5.37 | 69.3 |
| Ortho Vitros | | 5.06 | 65.3 |
| Roche Elecsys | | 5.78 | 74.6 |
| Siemens Advia Centaur | | 6.26 | 80.8 |

| T4 Bead Reconstitution Volume Combinations Tested on Beckman Coulter Access | | | |
|---|---|---|---|
| Reconstitution Vol (mLs) | Bead Number | Bead to Volume Ratio | T4 Recovery μg/mL |
| 10 | 1 | 0.1 | 1.08 |
| 5 | 1 | 0.2 | 2.04 |
| 2 | 1 | 0.5 | 5.24 |
| 5 | 2 | 0.4 | 4.4 |
| 2 | 2 | 1 | 11.04 |
| 10 | 3 | 0.3 | 3.5 |
| 5 | 3 | 0.6 | 6.4 |
| 5 | 4 | 0.8 | 8.56 |
| 3 | 4 | 1.33 | 14.3 |
| 2 | 3 | 1.5 | 16.24 |
| Recovery versus Ratio | Slope | 10.8 | |
| Recovery versus Ratio | Intercept | 0.0058 | |

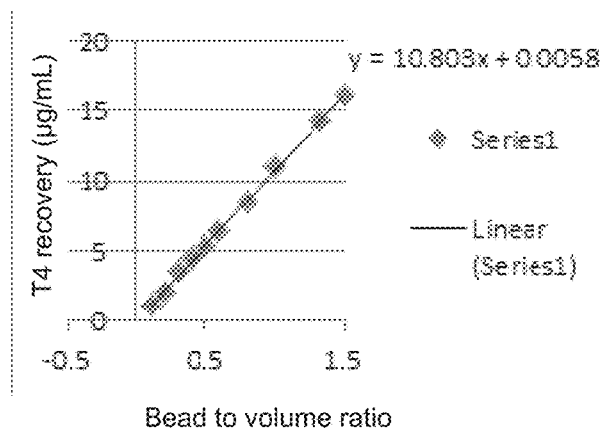

| | | | | | Correlation to Beckman Access | |
|---|---|---|---|---|---|---|
| Manufacturer /Instrument | # of Data points | Level 1 | Level 2 | Level 3 | Slope | Intercept |
| Beckman Coulter Access | 3361 | 5.16 | 10.6 | 15.31 | NA | NA |
| Siemans Centaur XP | 15292 | 6.11 | 12.47 | 16.77 | 1.05 | 0.87 |
| TOSOH AIA Models | 1997 | 5.43 | 10.46 | 14.69 | 0.91 | 0.74 |
| Roche Elecsys | 1787 | 5.84 | 11.15 | 14.74 | 0.88 | 1.47 |

*FIG. 10*

VALUE ASSIGNMENT FOR CUSTOMIZABLE QUALITY CONTROLS

CROSS-REFERENCE TO RELATED PATENT APPLICATIONS

The present patent application claims benefit of priority to U.S. Provisional Patent Application No. 62/041,398, filed on Aug. 25, 2014, which is incorporated by reference.

BACKGROUND OF THE INVENTION

Clinical diagnostics laboratories help healthcare professionals worldwide monitor the health and disease states of patients. These laboratories employ procedures to measure the concentration of one or more analytes, such as salts, sugars, proteins, hormones, or dissolved gasses, in a sample of tissue or bodily fluid obtained from an individual patient. The measured concentration of an analyte is compared with a threshold or range that distinguishes between normal and abnormal concentrations for the patient, with respect to the population to which the patient belongs. Based upon the comparison, additional tests can be prompted or a diagnosis for the patient can be made.

To ensure that analytical procedures are used to make accurate diagnoses, these procedures are calibrated with calibrators containing known and/or reproducible concentrations of certain analytes. For example, several calibrators containing different levels of an analyte can be used to construct a response curve of a particular instrument for that analyte. The concentration of the analyte in a patient sample can then be determined on the instrument by measuring the sample and interpolating along the response curve. Quality controls can also be used to test whether analyte concentrations reported by an instrument are consistent over time. An instrument can be tested periodically (e.g., daily or weekly) with a control and the historical distribution of reported analyte concentrations can be examined, for example using Levey-Jennings charts or Westgard rules. If a control measurement deviates significantly from recent measurements or the historical mean, then measurements of patient samples can be discontinued until the instrument can be serviced or recalibrated. Control measurements can be shared among laboratories to ensure that different instruments of the same design provide consistent results when used to detect the same analyte.

Commercially available quality controls are typically prepared by spiking one or more analytes into a base matrix containing various additives such as stabilizers and antimicrobial agents. Base matrices can be manufactured from processed human bodily fluids, such as urine or serum, to ensure similarity between the quality controls and patient samples. When multiple analytes are present, they can be for related medical conditions (for example, markers for different tumors) or detectable by the same method (for example, photometry). Quality controls are typically offered in bi-level or tri-level configurations to monitor and challenge the performance of a measurement procedure at analyte concentrations above, near, and/or below a decision threshold. Quality control materials are designed to be stable and cost-effective, and should provide lot-to-lot reproducibility for analyte test results.

Once a quality control for an analyte is prepared, a 'recovery' or reported concentration for the analyte can be determined by the end user or control manufacturer. The recovery is particular to the instrument or measurement procedure to which the control is applied, and can be stated as a mean or range. In the case of 'unassayed' controls, the end user determines recoveries using his or her own laboratory procedures or nationally or internationally recognized protocols, such as Clinical and Laboratories Standards Institute document C24-A33. Such protocols can involve testing the control on an instrument repeatedly over a short period of time (for example, 20 data points over two to three weeks) and computing the mean and standard deviation of recoveries measured during this time. For 'assayed' controls, the manufacturer provides expected means and ranges of recoveries for all analytes included in the control for one or more procedures. For this purpose, the control manufacturer tests a sufficiently large sample of each product lot with the measurement procedures to establish a statistically valid mean and standard deviation for the analyte at each level provided (FDA Guidance Document—Points to Consider Document on Assayed and Unassayed Quality Control Material, Draft Release Feb. 3, 1999). End users can also establish means and ranges for recoveries of assayed controls based on their own protocols prior to using the controls to monitor the performance of their test methods.

When a quality control is tested using multiple clinical diagnostic measurement procedures, the procedures can yield different recoveries for the same analyte. The differences can be due to differences or lack of standardization in assay architectures, detection technologies, or various parameters of the procedures. These differences can be difficult to reconcile, especially when no absolute standards for the analyte exist to provide well-known or 'true' concentrations. As a result, separate recovery ranges or thresholds must be established for each measurement procedure to identify normal and abnormal concentrations of the analyte in patient samples. The task of establishing these recoveries can be made more difficult when the concentrations of an analyte that are considered normal or abnormal vary. For example, one patient can be expected to have a higher concentration of an analyte in his or her bodily fluid than another patient, due to differences in the patients' ages, weights, ethnicities, general physiological states, or other factors. Thus, to make consistent diagnoses for many patients using multiple measurement procedures, recoveries of these procedures for the analyte often must be established at more than just two or three analyte levels.

Different diagnostic procedures often have different measurement ranges for a given analyte, and exhibit other differences in performance in terms of precision, accuracy, limits of quantitation (LOQ), limits of detection (LOD), or linearity. As a result, the procedures may not be amenable to monitoring with a common set of pre-prepared quality controls. Commercially available controls, for example those from Randox Laboratories Ltd. and Thermo Scientific, may not provide an analyte of interest in the concentrations needed to monitor all widely used diagnostic procedures for that analyte. Many instrument manufacturers provide their own quality controls for analytes to which their instruments are sensitive. But the controls for one instrument may not be usable on a competing instrument, again due to differences in instrument performance characteristics or detection technologies. In addition, the controls available from an instrument manufacturer may not contain a particular combination of analytes and other components found in a patient sample of interest.

Customizable quality controls are described in co-assigned U.S. Pat. No. 9,354,144, entitled "Customized Quality Controls for Analytical Assays" and issued on May 31, 2016, which is incorporated herein by reference. These quality controls can be prepared by dissolving one or more beads, each containing one or more analytes, in a liquid base matrix. By selecting the number of beads and the volume of base matrix, any desired analyte concentration can be obtained. Other desired components can be introduced into a control as part of the bead or matrix. With enough beads and base matrix, any number of controls corresponding to two, three, or more targeted analyte levels can be prepared. Customizable quality controls can thus be prepared according to the end user's needs and used to monitor any diagnostic procedure. Recoveries for these controls measured with different procedures can be compared.

BRIEF SUMMARY OF THE INVENTION

Provided herein are methods of preparing a quality control for an analyte according to a desired recovery, evaluating a predicted recovery of a measurement procedure that can be used to measure such a quality control, and determining the relative recoveries of two or more measurement procedures for an analyte.

In a first aspect of the invention, a method is provided for preparing a quality control for an analyte, wherein the quality control can be measured using a diagnostic measurement procedure, and the nominal concentration of the analyte in the quality control corresponds to a desired recovery of the measurement procedure for the analyte. The method includes: scaling the desired recovery by a correlation factor to estimate a target nominal concentration of the analyte in the quality control, wherein the correlation factor is based on data previously obtained using the measurement procedure; providing one or more solid beads containing the analyte, and a base matrix; determining a number of solid beads and a volume of the base matrix needed to prepare the quality control with the target nominal concentration of the analyte; and dissolving the number of beads in the volume of the base matrix, thereby preparing the quality control for the analyte.

In some embodiments, the method further includes designating one or more nearby recoveries, wherein each nearby recovery is at least 10, 20, or 50% above or below the desired recovery, and using interpolation, estimating nominal concentrations of the analyte corresponding to the nearby recoveries.

In some embodiments of the method, scaling the desired recovery by a correlation factor includes converting the desired recovery to a reference recovery, the reference recovery is an estimate of the recovery of a reference measurement procedure for the analyte, and the correlation factor is based on data previously obtained using the measurement procedure and the reference measurement procedure. In these embodiments, the method can also include designating one or more nearby reference recoveries of the reference measurement procedure, wherein each nearby reference recovery is at least 10, 20, or 50% above or below the reference recovery, and using interpolation, estimating nominal concentrations of the analyte corresponding to the nearby reference recoveries.

In a second aspect of the invention, a method is provided for evaluating a predicted recovery of a measurement procedure for an analyte, wherein the analyte occurs in a quality control, and the predicted recovery corresponds to the nominal concentration of the analyte in the quality control.

The method includes: determining a nominal concentration of the analyte in the quality control; scaling the nominal concentration by a correlation factor, wherein the correlation factor is based on data previously obtained using the measurement procedure, to obtain estimated predicted recovery of the measurement procedure for the analyte; testing the quality control using the measurement procedure, thereby obtaining a measurement response; determining an actual recovery of the measurement procedure for the analyte based on the measurement response; and comparing the predicted recovery with the actual recovery, thereby evaluating the estimated recovery of the measurement procedure for the analyte.

In some embodiments of the method, the quality control is prepared by adding a number of solid beads containing the analyte to a volume of a base matrix, and the nominal concentration of the analyte in the quality control is determined based on the number of beads and the volume of the base matrix.

In some embodiments, the method also includes designating one or more nearby concentrations of the analyte, wherein each nearby concentration is at least 10, 20, or 50% above or below the nominal concentration of the analyte in the quality control, and using interpolation, obtaining recoveries for the analyte at the nearby concentrations.

In some embodiments, the method also includes obtaining a range of recoveries of the measurement procedure for the analyte, wherein the range contains the predicted recovery.

In some embodiments of the method, scaling the nominal concentration by a correlation factor includes converting a reference recovery to the predicted recovery of the measurement procedure; the reference recovery is an estimate of the recovery of a reference measurement procedure for the analyte at the nominal concentration of the analyte in the quality control; and the correlation factor is based on data previously obtained using the measurement procedure and the reference measurement procedure.

According to a third aspect of the invention, a method is provided for determining relative recoveries of two or more measurement procedure for an analyte, wherein the analyte occurs in a quality control. The method includes: providing one or more solid beads containing the analyte, and a base matrix; dissolving a number of the solid beads in a volume of the base matrix to form a quality control; for each measurement procedure, testing the quality control, thereby obtaining a measurement response, and determining a recovery for the analyte based on the measurement response; and comparing the recoveries of the measurement procedure.

In some embodiments of the method, comparing the recoveries of the measurement procedures includes calculating a ratio of the recoveries.

In some embodiments, the method also includes: forming a reference quality control, wherein the nominal concentration of the analyte in the reference quality control is different from the nominal concentration of the analyte in the quality control; for each measurement procedure, testing the reference quality control, thereby obtaining a reference measurement response, and determining a reference recovery for the analyte based on the reference measurement response; and comparing the reference recoveries of the measurement procedures.

In embodiments of the preceding methods, the base matrix can be obtained from one or more patient samples.

BRIEF DESCRIPTION OF THE DRAWINGS

FIG. 4 shows a representative value assignment table provided with non-customizable quality controls.

FIGS. 7 and 8 show spreadsheets for predicting the recoveries of various measurement procedures for T4 thyroid hormone. Each spreadsheet allows the end user to input a number of solid beads and a volume of base matrix for a customizable quality control and receive recoveries, in µg/dL and nM, for each measurement procedure as an output.

FIG. 9 shows tables of predicted recoveries of various measurement procedures for T4 thyroid hormone in customizable quality controls.

FIG. 10 shows measured and predicted recoveries of the Beckman Access and other diagnostic instruments for T4 thyroid hormone in customizable quality controls.

DETAILED DESCRIPTION OF THE INVENTION

I. Introduction

Figure 1:
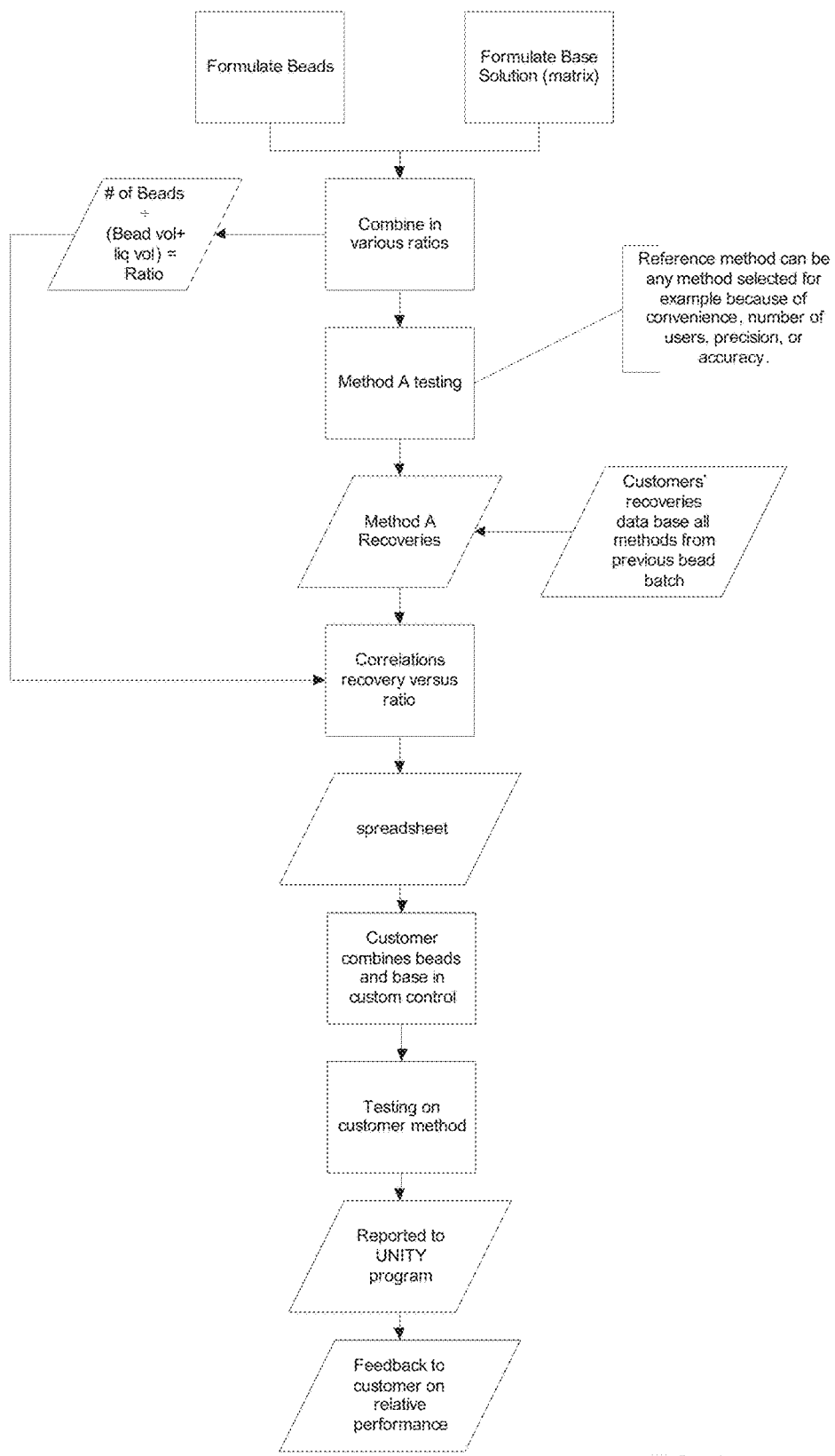
FIG. 1 is a flowchart illustrating embodiments of the methods described herein.

The present methods allow the end user of a diagnostic measurement procedure to prepare a customizable quality control for an analyte of interest according to a desired recovery for the analyte. Conversely, the methods allow the end user to predict the recovery of the procedure for the analyte when the procedure is used to assay a quality control already prepared. The quality control can contain one analyte or many analytes, as well as a human bodily fluid or components thereof, and can be used to monitor the measurement procedure for patient samples.

Each quality control is prepared by dissolving one or more solid beads containing an analyte of interest in a liquid base matrix. This process is described in related U.S. Pat. No. 9,354,144 referenced above, as well as below under "Customizable Quality Controls". The concentration of the analyte in the quality control is estimated from the number of beads and the volume of base matrix. Generally, a larger number of beads or a smaller volume of base matrix results in a higher analyte concentration. The analyte concentration in a particular quality control, corresponding to a given number of beads and volume of base matrix, can be estimated to an absolute level (for example, in units such as g/l, U/l, or micromolar), or relative to controls prepared with other numbers of beads or volumes of base matrix.

To determine the number of beads and volume of base matrix needed for a desired recovery, or conversely predict the recovery corresponding to a number of beads and volumes of base matrix, reference is made to data previously obtained using the end user's chosen measurement procedure or other procedures. The data can reflect the different performance characteristics of various procedures, such as measurement range, precision, accuracy, limits of detection, limits of quantitation, and linearity. Alternatively or in addition, the data can be specific to the end user's analyte of interest or related analytes. For example, the data can include: recoveries of a procedure at various relative or nominal concentrations of the analyte; recoveries of a measurement procedure at a fixed nominal concentration of the analyte when the analyte is suspended in various base matrices; recoveries of multiple measurement procedures for the analyte when measured at the same nominal concentration or set of bead-to-volume ratios; or recoveries of one or more measurement procedures for multiple analytes, including the analyte of interest, when these analytes are present together in the same control or sample at various relative or nominal concentrations.

The previously obtained data can be embodied in a computer program or spreadsheet, where the user can input a nominal analyte concentration (or number of beads and volume of base matrix needed to obtain this concentration) and receive a recovery as output, or vice versa. By making reference to previously obtained data, the end user can account for biases between the nominal concentration of the analyte in the quality control and the recovery reported by the procedure of interest, sensitivity of the recovery to the concentrations of other components of the quality control, and differences in the recoveries reported by different procedures. Thus, the user can establish an accurate correspondence between the nominal concentration of the analyte in the quality control and the expected recovery of the user's chosen measurement procedure for the analyte. From this correspondence, the user can prepare a quality control for which the measurement procedure gives a desired recovery, or predict the recovery for a quality control already prepared.

The present methods thus provide a way to prepare a quality control for an analyte of interest, to be used in conjunction with a desired measurement procedure where the analyte is present at a targeted or diagnostically relevant level. This level can be above, near, or below a medical decision point for the analyte in a particular patient population, or fall within a range considered normal or abnormal for the population. Each quality control can be customized to the targeted analyte level with high precision, and any number of quality controls corresponding to multiple levels can be prepared. Quality controls that have well-established or predictable recoveries at these levels can be used to monitor the procedure for testing patient samples by checking for consistency of the procedure over time.

The present methods are not limited to a particular kind of analyte or a particular measurement procedure. In fact, customizable quality controls as described herein can contain any desired analytes and be prepared or measured using any appropriate measurement procedures. These quality controls thus afford greater flexibility than the non-customizable quality controls provided by instrument manufacturers, allowing the performance of many instruments and measurement procedures to be monitored.

II. Definitions

'Sample' refers to a biological sample obtained from one or more organisms, living or dead. In embodiments of the present invention, a sample can be obtained from a single human subject, such as a subject diagnosed with a disease, a subject suspected of suffering from a disease, or a subject known or suspected to not suffer from a disease. 'Human subject' and 'patient' are used interchangeably herein, and 'patient sample' refers to a sample obtained from a patient. A sample can be obtained from or constitute a tissue or bodily fluid. Examples of human bodily fluids that can serve as samples, or from which samples can be obtained, include blood, serum, urine, mucus, saliva, semen, vaginal fluid, synovial fluid, or cerebrospinal fluid.

'Analyte' refers to an ionic, molecular, or supramolecular species that is present in a sample and can be detected. Examples of analytes include ions, gasses, small organic molecules, small inorganic molecules, proteins (e.g., enzymes or antibodies), lipids, carbohydrates, nucleic acids, membranous structures, organelles, and cells.

'Base matrix' refers to a material initially devoid, or largely devoid, of an analyte but to which the analyte can be added. Upon addition, the analyte can be dissolved or suspended in the base matrix. A base matrix can be a biological sample, such as a tissue or bodily fluid, exclusive of the analyte or from which the analyte has been removed. Alternatively, a base matrix can contain select components of a tissue or bodily fluid. In some embodiments of the present invention, a base matrix is liquid and homogeneous.

'Concentration' refers to the quantity of an analyte per unit volume of a material. The material can be a biological sample, a base matrix, a liquid, solid, gas, or any other medium. Concentration can be expressed in any desired units, for example grams per liter (g/l), moles per liter (molar, denoted by 'M'), or activity units per liter (U/l).

'Nominal concentration' refers to the estimated concentration of an analyte in a material. Nominal concentration can be determined using accepted methods in the diagnostic arts or as desired. For example, the concentration of an analyte in sample can be estimated gravimetrically or from a series of tests using an accepted reference procedure. When beads containing an analyte are dissolved in a base matrix, the concentration of the analyte in the resulting solution can be estimated from the number of beads dissolved, the mass of each bead, the mass or activity of the analyte in each bead, and/or the volume of base matrix. The concentration can also be estimated from the ratio of the number of beads to the volume of base matrix, termed the 'B/MV ratio' herein.

'Quality control' refers to a mixture of an analyte and a base matrix. The mixture can be used to monitor the performance of one or more measurement procedures, and the analyte is present in the mixture at a known, predetermined or reproducible nominal concentration.

'Measurement procedure' refers to a technique or system for detecting and estimating the concentration of an analyte in a sample or quality control. A measurement procedure can encompass an instrument or manual method and procedures for calibration or operation.

'Recovery' refers to the concentration of an analyte in a sample or quality control as reported by a measurement procedure. A recovery can be stated as a single value, such as may be obtained from a single measurement. Alternatively, a recovery can be stated as a mean value, reflecting multiple measurements, and/or a range. The range can represent the minimum and maximum of many measurements, the mean plus or minus the variance, standard deviation, or standard error of these measurements, or any other appropriate set of values reflecting statistical variation or uncertainty.

'Medical decision point' refers to the concentration of an analyte in a patient sample that serves as the threshold or cutoff for a medical decision. The medical decision can be deciding whether the concentration of the analyte is normal or abnormal (e.g., abnormally high or abnormally low), diagnosing the patient with a disease, or requesting that the patient get further tests, for example. Generally, different medical decisions are made depending on whether the recovery of the analyte in the patient sample is above or below the medical decision point. A medical decision point can be an absolute concentration, a relative concentration, or an approximate concentration or range of concentrations. A medical decision point can be expressed as a recovery measured using a particular measurement procedure.

'Level' refers to the concentration or abundance of an analyte in a patient sample or quality control. A level can be stated as a single value or as a range. Alternatively or in addition, a level can be characterized by its relationship to (e.g., above, below, near, overlapping with, or representative of) another level, a medical decision point, or a health condition.

The terms 'about' and 'approximately equal' are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

'Percent above' or 'X % above', where 'X' is a number, refers to the difference between two numerical values. A is said to be X % above B if A is greater than or equal to the sum of B and X % of B. The terms 'percent below' and 'X % below' are used likewise. For example, A is said to be X % below B if A is less than or equal to X % of B subtracted from B.

III. Customizable Quality Controls

The customizable quality controls discussed herein can be prepared by dissolving one or more solid beads, each containing one or more analytes, in an aqueous base matrix. These controls can be prepared by the user at the point of use and enable the user to select the analyte(s) that the controls contain, the number of control levels, the concentration of analyte in each control, the base matrix, and other factors affecting the utility of the controls for particular assays. The term "bead" is used herein to denote spheres, pellets, or any solid bodies of similar size, i.e., capable of being packaged in a bottle, for example, and used either individually or in small quantities. In addition to the analyte, individual beads can contain a bulking agent to add structural integrity, plus other optional components to help control the characteristics and quality of the control as it is reconstituted. The base matrix is an aqueous solution of a salt and a buffer at a pH of about 4.0 to about 9.0, either in a human biological fluid or in water, and if in water, the solution preferably also contains human or animal source materials that provide the matrix with the attributes of a biological sample. The beads and the base matrix can be shipped and sold separately or as parts of a kit, and they can be combined at the site of use immediately prior to their use, or combined by the purchaser and stored for later use. Uncombined, the beads and matrix can be shipped and stored without special maintenance conditions such as refrigeration or freezing.

The solid beads, which are soluble in water, can conveniently be manufactured as spheres. Provided the sizes of the spheres are uniform, these sizes are not critical to the utility or novelty of the invention, and can vary. In many cases, spheres having diameters within the range of from about 3 mm to about 10 mm will be convenient to use. For controls to be used for single-analyte assays, each bead in certain embodiments of the invention will contain the single analyte as the only biologically derived species in the bead, and controls of different nominal concentrations of that analyte can be obtained by dissolving different numbers of beads in separate and either equal or unequal volumes of base matrix. Controls can also be formulated for multi-component assays, i.e., assays for two or more analytes, either for simultaneous detection or in separate detections, by including the two or more analytes in the beads. Here as well, controls of different levels of concentration of both analytes can be obtained by dissolving different numbers of beads in different aliquots of the same volume of the base matrix. Controls for multi-component assays can also be prepared from beads with a single analyte per bead by combining beads of different analytes in a single volume of the base matrix, thereby allowing the user greater flexibility in the design and use of the controls. A set of different levels of each analyte can be achieved by using different numbers of beads in separate but equal volumes of the base matrix, or the same number of beads in different volumes of the base matrix.

The quantity of analyte per control can vary widely and will be governed by the volume of the reconstituted control and the minimum number of beads to be used per control. For example, a given set of controls may include three levels of analyte, and the quantity of analyte in a single bead may thus be such that the control with the lowest analyte level can be achieved by reconstituting a single bead in a volume of base matrix. The number of levels that the user will prepare in forming the control set can also vary, and in some cases as little as two levels will suffice. In most cases, however, controls constituting three or more analyte levels will be prepared, thereby allowing the user to check for linearity of the assay response, and to have controls representing levels approximately equal to the decision point as well as above and below.

In certain embodiments, the beads will contain a single analyte and no additional species other than formulation adjuvants, which are materials included to dilute the analyte in the bead or to enhance or modify the physical characteristics of the bead and the ability of the bead to dissolve or disperse rapidly in the base matrix. Formulation adjuvants may serve, for example, to maintain the physical integrity of the bead during storage, shipment, or handling, to impart chemical stability to the bead, the analyte, or both while still in bead form, to maintain the ionic strength or the pH of the reconstituted control once the bead is dissolved in the base matrix, or to give the reconstituted control the attributes of a human sample in any of various respects that do not interfere with the ability to detect the analyte. Certain beads may contain two or more analytes, although beads that are limited to a single analyte can offer greater flexibility in their use as they are reconstituted as controls, since controls with two or more analytes can be prepared by combining different beads with single analytes each, allowing the laboratory technician to control or vary the relative amounts. Optimal formulating adjuvants are those that do not interfere with the detection of the analytes in the reconstituted controls, by either masking the analytes, being detected in combination with the analytes in a manner that does not permit segregation of the detection of one analyte from another, or in any way affecting the sensitivity of the assay toward the analyte One type of formulation adjuvant is a bulking agent. One or more bulking agents will provide physical integrity to the bead by helping the bead hold its shape. Conventional materials that are known to achieve this effect can be used. Examples of bulking agents are glycine, sorbitol, mannitol, lactose, dextrose, albumin, ovalbumin, gelatin, polysaccharides such as dextran, and hydrophilic polymers such as polyvinylpyrrolidone. Bovine serum albumin is particularly convenient in many cases. The appropriate volume of bulking agent will be readily apparent to those of skill in bead formulation, and actual values are not critical to the novelty or utility of the invention. When beads are formed by lyophilization of aqueous solutions, for example, the solution prior to lyophilization in many cases will contain from about 0.3 g to about 3 g of bulking agent per deciliter of solution.

Another type of formulation adjuvant is a salt, which can be included to maintain the ionic strength of the base matrix when the beads are dissolved in the matrix. The optimal quantity of salt in the bead will thus be that amount that will produce at most a minimal difference between the salt concentration of the base matrix and that of the reconstituted control. Again using as examples beads that are formed by lyophilization of aqueous solutions, the salt concentration of the aqueous bead solution prior to lyophilization may range from about 10 mM to about 300 mM. The salt itself can be any salt that is compatible with biological samples and that behaves in the same way in a control as it does in the sample to be assayed. Sodium chloride is a common salt for this type of use.

A third type of formulation adjuvant is a buffer to maintain the reconstituted control at a desired pH. The pH of the bead can vary widely as evidenced by the range quoted above, but for controls for typical assays of human and other mammalian subjects, the pH will generally range from neutral to slightly basic. In many cases, an optimal pH level will be within the range of from about 6.2 to about 8.5. Examples of suitable buffers are tris(hydroxymethyl)aminomethane (Tris base), tris(hydroxymethyl)aminomethane hydrochloride (Tris-HCl), bis(2-hydroxyethyl)iminotris-(hydroxymethyl)methane (Bis-Tris base), bis(2-hydroxyethyl)iminotris-(hydroxymethyl)methane hydrochloride (Bis-Tris-HCl), and N-2-hydroxyethyl-piperazine-N-2-ethanesulfonic acid (HEPES).

Beads can be prepared by any conventional means, most convenient of which is by lyophilization from an aqueous solution in which the components of the ultimate bead are dissolved. The volume of the solution prior to freezing and sublimation can vary widely, although in most cases a volume ranging from about 5 μL to about 1,000 μL will provide the best results. Lyophilization avoids or minimizes degradation of the bead components due to exposure of the bead to elevated temperatures.

The human or biological source materials that are included in the base matrix in certain embodiments of this invention can be human serum albumin, bovine serum albumin, or any other albumin or protein in general that is analogous to human serum albumin. When human serum albumin or bovine serum albumin is also included in the bead(s) as a bulking agent, its concentration is preferably low enough that the dissolving of the bead in the base matrix does not result in a reconstituted control with a concentration that is substantially different from that of the base matrix prior to reconstitution. Thus, when the bulking agent in the bead is bovine serum albumin (BSA) and the additive in the base matrix is human serum albumin (HSA), the concentration of BSA in the aqueous solution from which the bead is formed (by lyophilization, for example) may be one-tenth to one-third, for example, of the concentration of HSA in the base matrix.

The base matrix can be provided with an osmolarity that provides a reconstituted control that most closely resembles the samples that are to be assayed. With these considerations in mind, osmolarity levels can vary widely, although in most cases best results will be achieved with an osmolarity within the range of from about 50 mOsm/kg to about 1,000 mOsm/kg. Osmolarity can be controlled by the inclusion of a salt, as in the beads themselves. The same types of salts can be used in both, again with sodium chloride as a convenient example. The base matrix can also be provided with a buffer, conveniently using the same buffer as in the beads.

The base matrix can also be prepared from human and animal source materials that have been treated to remove endogenous analytes that might interfere with particular assays. Examples of these source materials are human whole blood, plasma, serum, urine, and oral and synovial fluid. Endogenous analyte removal can be achieved by filtration, precipitation, decomposition by enzymatic and heat treatment, and chromatographic separations such as affinity separations, ion exchange, and size exclusion.

If desired, the base matrix can be obtained from one or more patient samples. For example, two or more patient samples can be pooled to obtain a base matrix. The same sample(s) can provide a base matrix for one or more quality controls and be subjected to diagnostic tests.

Further optional components of the base matrix are stabilizers and antimicrobial agents. Examples of stabilizers are protease inhibitors, chelating agents, cryoprotectants, reducing agents, and surfactants. Examples of antimicrobial agents are sodium azide, ciprofloxacin, chloramphenicol, gentamicin, amikacin, tobramycin, and amphotericin B. Appropriate amounts of these additives will be readily apparent to those of skill in their use.

IV. Methods

The methods provided herein allow the end user of a diagnostic measurement procedure to a compute a relationship between the nominal concentration of an analyte in a quality control and the recovery of the procedure for the analyte when used to measure the quality control. Thus, the end user can prepare a quality control having a desired recovery, or predict the recovery for a quality control already prepared. The quality control can be prepared by dissolving one or more solid beads in a base matrix, as described above.

A first method is provided for preparing a quality control for an analyte, where the quality control can be measured using an measurement procedure, and the nominal concentration of the analyte in the quality control corresponds to a desired recovery of the measurement procedure for the analyte. The method includes scaling the desired recovery by a correlation factor to determine a target nominal concentration of the analyte in the quality control The nominal concentration can be expressed, for example, as the number of beads per unit volume of base matrix.

In this method and the other methods discussed below, any procedure that can be used to detect analytes in a biological sample can serve as the measurement procedure. Commercially available instruments and systems used for diagnostics and analyte detection include, but are not limited to, Abbott Architect, Alfa Wasserman ACE, Beckman Coulter Unicel, Beckman Coulter Access, Biomerieux Vidas, Ortho Vitros, Roche Elecsys, Siemens Centaur, and Tosoh AIA. The procedure can also include a conventional laboratory instrument, such as a spectrophotometer, that has been adapted or customized to detect an analyte. The measurement procedure can detect only one analyte of interest or other analytes and species too, and can make use of any technologies or phenomena to perform detection. For example, detection can be based on optical absorbance, electrical conductivity, magnetism, radioactivity, fluorescence, chemiluminescence, electroluminescence, enzymatic activity, antibody-antigen binding, or calorimetry. Other means of detection will be apparent.

The correlation factor reflects the tendency of the procedure to report recoveries for the analyte of interest that differ from the nominal concentration of this analyte in a sample or quality control, when the nominal concentration can be well known. Put differently, the correlation factor accounts for the recovery overestimating or underestimating the concentration of the analyte. When the nominal analyte concentration in a quality control is expressed in different units from the recovery, the correlation factor can also serve to transform the recovery into units of concentration (for example, a ratio of the number of beads to the volume of base matrix, also called the B/MV ratio). The correlation factor captures the sign and degree of the expected difference between the desired recovery and target nominal concentration of the analyte. In some embodiments, scaling the desired recovery to estimate the concentration involves multiplying the desired recovery by a scalar quantity. For example, if a recovery of 100 µg/mL for a certain analyte is desired, but the measurement procedure is known to overestimate the analyte concentration in quality controls by a factor of 1.1, then the recovery can be scaled down by this factor to obtain a target nominal concentration of 100/1.1=90.9 µg/mL. More generally, scaling the desired recovery by the correlation factor involves applying a function to the desired recovery to return the nominal concentration. The function can be a linear, quadratic, cubic, exponential, logarithmic, or power function, for example, and can include a constant term that is added to or subtracted from the desired recovery.

The correlation factor is based on data previously obtained using the measurement procedure. The previous data can be obtained on the same instrument or multiple instruments, and can reflect variability of recovery over time or among instruments. The data can be solicited from multiple labs (for example, by sending each lab the same sample, standard, or quality control) or be obtained through collaborations between labs (for example, through the Bio-Rad UNITY Interlaboratory Program). Regression analysis can be applied to the previous data to obtain a correlation factor appropriate for a desired analyte recovery or nominal analyte concentration. For example, a regression line can be fitted to a plot of analyte recovery versus nominal analyte concentration, and the correlation factor can be obtained from the fit function, or by reading values from the regression line. Other regression methods appropriate for the numerical relationship between analyte recovery and nominal analyte concentration can be employed.

In some embodiments, the previous data are obtained from end users of the measurement procedure testing quality controls, which are prepared as described herein by dissolving beads containing the analyte in a base matrix. Thus, correlations between analyte recovery and nominal analyte concentration are established empirically and can be updated over time (FIG. 1). The previous data can correspond to quality controls prepared from a particular lot or batch of beads, for example beads belonging to the same lot as those being used by the end user to carry out the present method, or to the most recently manufactured lot of beads. Similarly, the previous data can correspond to quality controls prepared from a particular lot, batch, or kind of base matrix.

Figure 2:
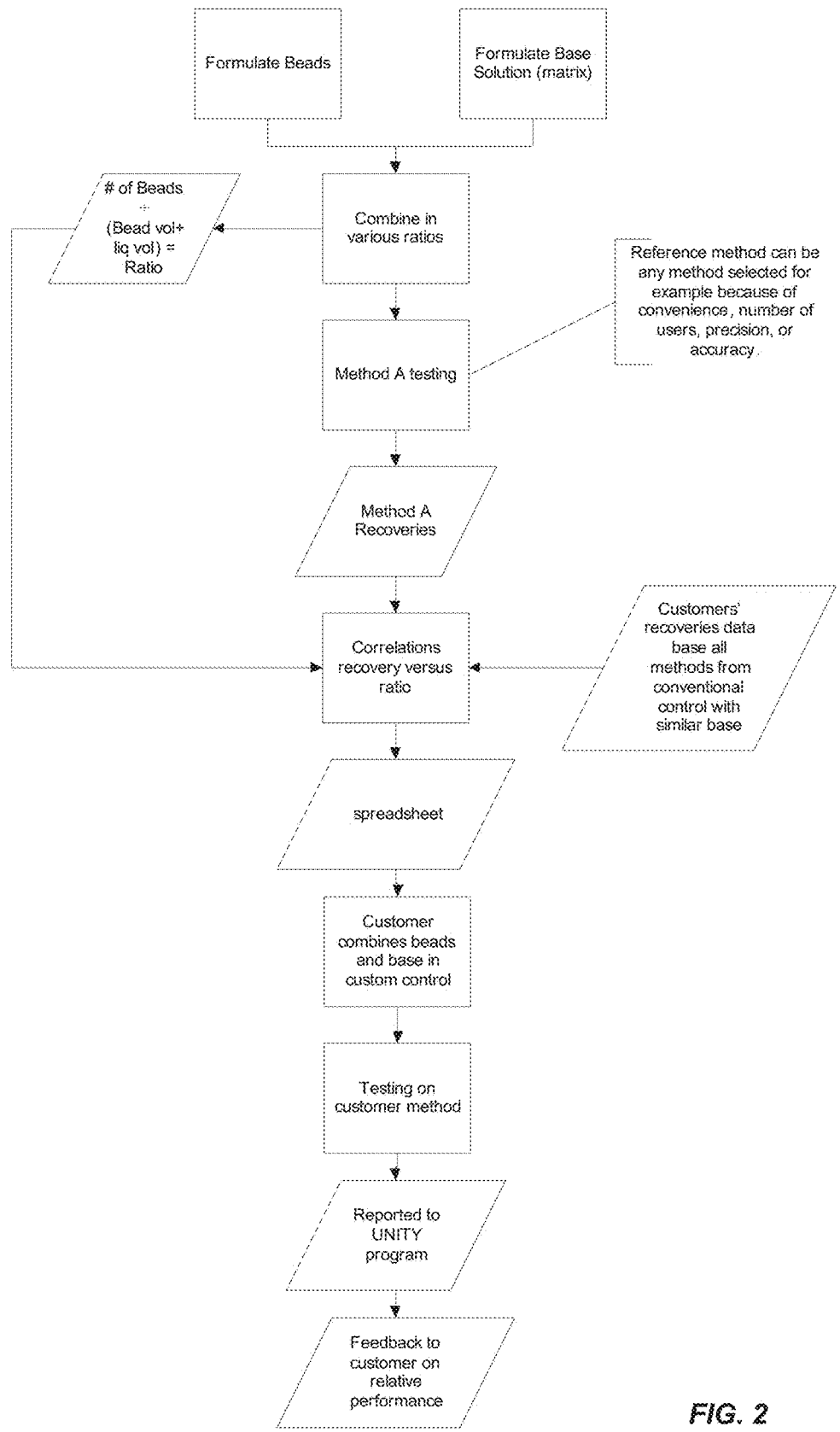
FIG. 2 is a flowchart illustrating embodiments of the methods described herein.

In some embodiments, the previous data on which the correlation factor is based are obtained by testing non-customizable quality controls (FIG. 2). These quality controls can have fixed nominal analyte concentrations and can be provided pre-prepared to end users of the measurement procedure. The previous data can be obtained from end users of the measurement procedure. It will be recognized that, to calculate an accurate correlation factor from these data, the base matrix used in the non-customizable quality controls should be similar in composition to that with which the quality control in the present method will be prepared.

The end user of the analysis program can apply the correlation factor by entering the desired recovery into a computer program or spreadsheet. The computer program or spreadsheet can also house data previously obtained using the measurement procedure, and calculate the correlation factor based on the input information and other data. The user can then receive, as an output from the program, a nominal concentration of the analyte corresponding to the desired recovery.

Once a target nominal concentration of the analyte in the quality control has been determined (expressed, for example, as a B/MV ratio), the quality control can be prepared using one or more solid beads containing the analyte, and a base matrix. Specifically, a number of solid beads is dissolved into a volume of the base matrix, as described above ("Customizable Quality Controls"), so that the analyte is present in the resulting solution (i.e., the quality control) at the target nominal concentration. Any of the various embodiments of the solid beads and base matrix described above, and combinations thereof, can be provided for this purpose. For example, the solid beads can contain bulking agents, and the base matrix can be an aqueous solution containing components of a human bodily fluid.

In some embodiments, the solid beads and base matrix are supplied along with software used to compute the correlation factor and determine the target nominal concentration of the analyte. The software can then be used to determine a number of solid beads and a volume of base matrix consistent with the target nominal concentration. For example, information about a particular lot of solid beads and/or base matrix, such as the amount (mass or mole quantity) of analyte per bead, the variability in this amount, or the nominal concentrations of adjuvants in the beads and base matrix, can be incorporated into the software, so that a number of solid beads and a volume of base matrix are returned to the end user along with the target nominal concentration. Alternatively, the software can let the end user provide this information as one or more inputs. If desired, the software can take into account the volume displaced by the solid beads, and accordingly correct the recommended number of solid beads and volume of base matrix needed to prepare the quality control with a desired recovery. The end user can also calculate a number of solid beads and a volume of base matrix needed for the quality control by hand, with knowledge of the amount of analyte per bead and the target nominal concentration of the analyte. It will be recognized that different numbers of beads and volumes of base matrix can be used to prepare the quality control, because the analyte concentration in the quality control is determined by the ratio of these quantities.

Some embodiments of the method also include designating one or more nearby recoveries, each at least 10, 20, or 50% above or below the desired recovery, and estimating concentrations of the analyte corresponding to the nearby recoveries. These steps can be used to prepare additional quality controls representing different levels of analyte. For example, if the desired recovery corresponds to an intermediate level of the analyte, or a normal level in a particular patient population, then the nearby recoveries can correspond to low, high, abnormally low, or abnormally high levels of the analyte. Thus, additional quality controls corresponding to the nearby recoveries can be used to identify abnormal or disparate analyte concentrations in patient samples.

When one or more nearby recoveries are designated, the corresponding analyte concentrations are estimated in the same manner as that for the desired recovery. That is, each nearby recovery is scaled by a correlation factor according to data previously obtained using the measurement procedure. The nearby recoveries can fall in different portions of the measurement range of the measurement procedure from the desired recovery and from each other. Thus, the correlation factors can be obtained by interpolating between points in the previously obtained data.

In some embodiments, scaling the desired recovery by a correlation factor includes converting the desired recovery to a reference recovery. The reference recovery is an estimate of the recovery of a reference measurement procedure (optionally designated 'Procedure B') for the analyte. The correlation factor is based on data previously obtained using the reference procedure, i.e., Procedure B, in addition to data for the end user's chosen procedure. The correlation factor can thus reflect how recoveries of the two measurement procedures compare under comparable conditions. In any embodiment of the methods discussed herein, a measurement procedure may designated as a reference procedure for any reason, including acceptance by experts, ease of use, number of users, precision, or accuracy.

Figure 3:
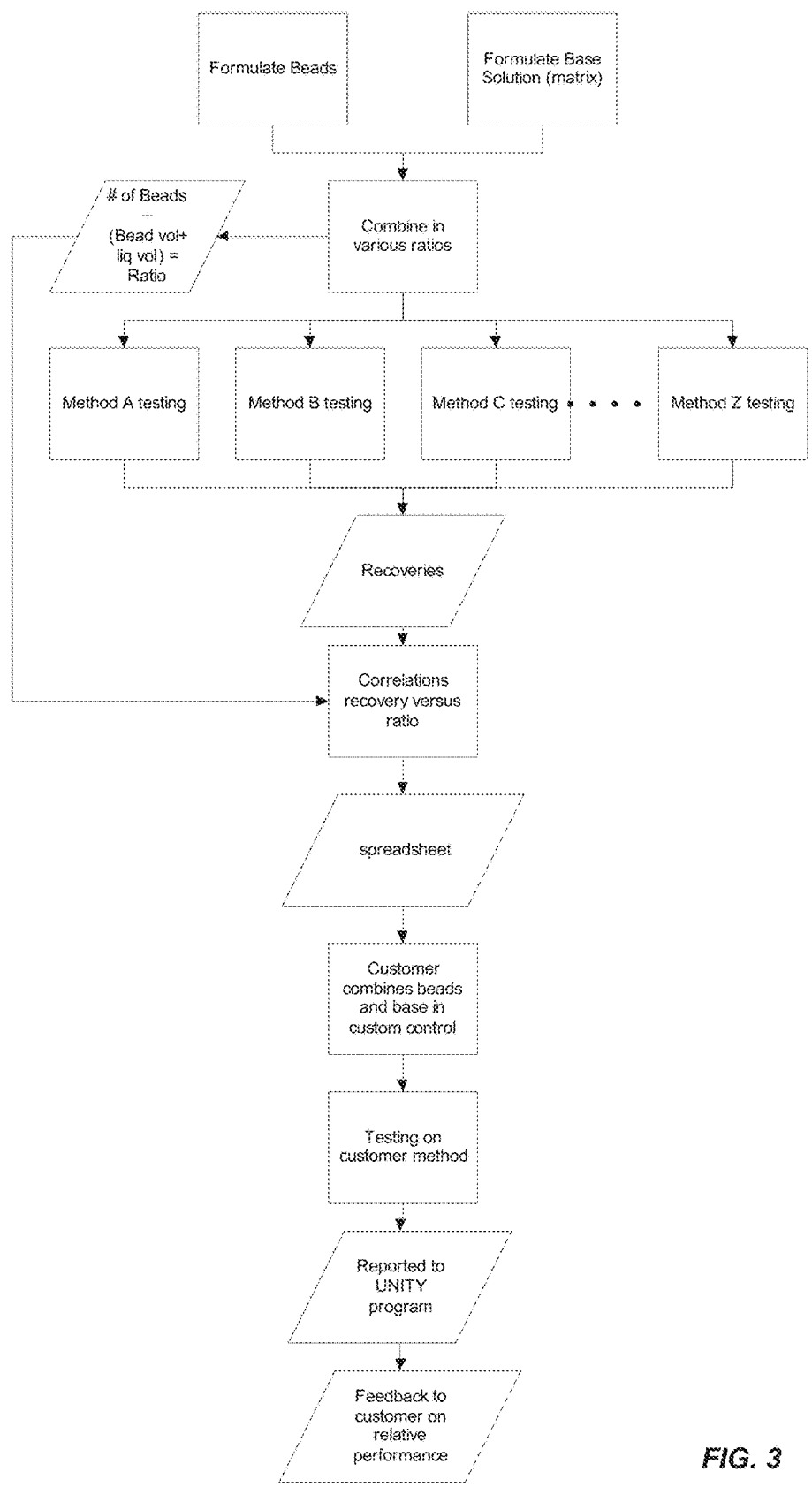
FIG. 3 is a flowchart illustrating embodiments of the methods described herein.

As appropriate, data previously obtained for any two procedures can be compared or contrasted to calculate the correlation factor, with either procedure serving as the reference procedure. If desired, data from additional reference procedures (e.g., Procedures C or D) can be included in the calculation (FIG. 3). The calculation can include performing regression analysis to establish numerical relationships among the recoveries reported by the two or more measurement procedures. For example, the recoveries reported by two measurement procedures can be displayed on a plot such that recoveries reported by the first measurement procedure are plotted on the x-axis and recoveries reported by the second measurement procedure are plotted on the y-axis. Thus, each point on the plot represents testing a nearly identical quality control with the two procedures, and the different points can represent different nominal analyte concentrations. A regression line can then be fitted to the plot to provide the recovery of one procedure as a function of recovery of the other procedure. The data used to calculate the correlation factor can be obtained as desired, for example by the manufacturer of the beads and base matrix used to prepare customizable quality controls, or by end users of the measurement procedures. In embodiments where the correlation factor is based on data previously obtained using more than one measurement procedure, one or more nearby reference recoveries can be designated, in analogy to the nearby recoveries discussed above.

The quality controls discussed herein need not be prepared in view of desired recoveries for the analytes they contain. To the contrary, quality controls can be prepared and measured using an measurement procedure without targeting specific recoveries beforehand. This can be done, for example, when the measurement range of the measurement procedure is being tested for linearity, or when the nominal concentrations of an analyte in a series of quality controls are set by convenience (e.g., 1, 2, or 3 beads dissolved in the same volume of base matrix). However, it can also be useful to estimate the recovery of a measurement procedure to quantify the relationship between the nominal concentration and recovery of the analyte.

A second method is provided herein for evaluating a predicted recovery of an measurement procedure for an analyte, where the analyte occurs in a quality control or linearity set, and the estimated recovery corresponds to the nominal concentration of the analyte. The method includes determining a nominal concentration of the analyte in the quality control. The nominal concentration can be in any units, and can be absolute or relative to another quality control or reference. In embodiments where the quality control is prepared by adding a number of solid beads containing the analyte to a volume of a base matrix, the nominal concentration of the analyte in the quality control can be determined based on this number. For example, the nominal concentration can be determined by dividing the total amount of analyte (calculated as the amount of analyte per bead times the number of beads) by the volume of base matrix. Alternatively, the nominal concentration can be expressed simply as the B/MV ratio. If desired, the nominal concentration can be corrected for the excluded volume of the beads.

Once determined, the nominal concentration is scaled by a correlation factor, which is based on data previously obtained using the measurement procedure, to obtain an predicted recovery of the measurement procedure for the analyte. The correlation factor is similar to the correlation factor discussed above for the first method, but provides analyte recovery as a function of nominal concentration, rather than nominal concentration as a function as recovery. In cases where the correlation factor is a single scalar quantity, the correlation factor for the present second method can be the reciprocal of the correlation factor for the first method. For example, if previous data indicate that a measurement procedure reports a recovery in excess of the nominal concentration of an analyte by a factor of 1.1, then the nominal concentration can be multiplied by a correlation factor of 1.1 to obtain the predicted recovery. The present correlation factor generally reflects the tendency of the recovery to overestimate or underestimate the approximate analyte concentration in the quality control, or any other systematic disagreement between these variables. The correlation factor can also reflect any difference in units between the recovery and nominal concentration.

The correlation factor can be calculated as desired based on data previously obtained using the measurement procedure. For example, the correlation factor can reflect varying performance of the procedure in different parts of its measurement range, and sensitivity of the procedure to the nominal concentrations of other analytes or solutes. The correlation factor can be general to test methodologies that can be performed on many instruments, or specific to a methodology as performed on a particular instrument. Other considerations for calculating the correlation factor will be apparent in view of the discussion above. For example, regression analysis can be performed on recovery data previously obtained at many nominal analyte concentrations, in order to calculate a correlation factor at the particular nominal analyte concentration in the end user's quality control. As for the first method, the correlation factor can be calculated in software by inputting this nominal analyte concentration, or the number of beads and volume of base matrix used to prepare the quality control.

Evaluating the predicted analyte recovery for the quality control further includes determining an actual recovery. First the quality control is tested using the measurement procedure to obtain an instrument measurement response. Next, an actual recovery of the measurement procedure for the analyte is determined based on the measurement response. The measurement can be made as appropriate for the measurement procedure or instrumentation associated with the procedure, and can involve blanking or other preliminary steps. The actual recovery can be determined automatically from the measurement, for example as a read-out from an instrument, or can be calculated by the end user using an observable from the measurement. Observables can be binary (the presence or absence of a signal), qualitative, or quantitative. Examples of observables include but are not limited to optical absorbance, fluorescent emission, enzymatic activity, and radioactivity.

To complete the evaluation of the predicted recovery of the measurement procedure for the analyte, the predicted recovery is compared with the actual recovery. Comparing these recoveries can include calculating a ratio or difference, or simply noting which recovery is larger or smaller. The comparison can be made in software or by the end user. The results of the comparison can be used as desired by the end user or others, for example to monitor the measurement procedure or prepare additional quality controls.

Some embodiments of the present method also include designating one or more nearby concentrations of the analyte, for example each at least 10, 20, or 50% above or below the nominal concentration of the analyte in the quality control, and obtaining predicted recoveries for the analyte at the nearby concentrations. The nearby concentrations can correspond to quality controls that are prepared in addition to that for which the nominal analyte concentration is determined and the recovery is predicted. Alternatively, the nearby concentrations can be designated simply by scaling, adding to, or subtracting from the determined concentration and need not correspond to actual quality controls. Recoveries for the analyte at the nearby concentrations can be predicted by scaling each nearby concentration by a correlation factor as discussed above. The correlation factors can be obtained by interpolating between points in previously obtained data.

In some embodiments, when an analyte's nominal concentration in a quality control is known and is scaled by a correlation factor, a range of recoveries is obtained in addition to a single value. The range can contain the predicted recovery and reflects the practice followed by many laboratories of reporting a range of recoveries for each analyte level or quality control. In these embodiments, the predicted recovery can be a mean of the expected recoveries, and the range can be a measure of spread or uncertainty in the expected recoveries, such as standard deviation.

In some embodiments, scaling the nominal concentration by a correlation factor includes converting a reference recovery to the predicted recovery of the measurement procedure. Here, the reference recovery is an estimate of the recovery of a reference measurement procedure ("Procedure B") for the analyte at the nominal concentration of the analyte in the quality control. Thus, the recovery is predicted in a two-step process, where the analyte's nominal concentration is first likened to a reference recovery (i.e., the recovery of Procedure B) and the reference recovery is then converted to a predicted recovery for the end user's measurement procedure of interest. The correlation factor can be based on data previously obtained using both measurement procedures, as discussed above, and can capture how recoveries reported by the two procedures compare under comparable conditions. The correlation factor can include or be calculated using any function (e.g., linear or quadratic) that relates the reference recovery to the predicted recovery. More than one measurement procedure can serve as a reference measurement procedure to relate the recoveries of various measurement procedures to each other. It will be recognized that accurate correlation factors can be more easily calculated if the measurement procedure and reference measurement procedure(s) have similar measurement ranges.

In order to determine correlation factors, and for any other desired purposes, a third method is provided herein for determining relative recoveries of two or more measurement procedures for an analyte, where the analyte occurs in a quality control. The method includes preparing a quality control using solid beads and a base matrix. First, one or more solid beads containing the analyte, and a base matrix, are provided. Next, a number of the solid beads is dissolved in a volume of the base matrix to form the quality control. These steps are described in greater detail above. The solid beads and base matrix can have any of the attributes discussed above, and the quality control can contain any analyte or analytes.

Once the quality control is prepared, it is used to determine relative recoveries of the two or more measurement procedures. For each measurement procedure, the quality control is tested, and a recovery for the analyte is determined based on the instrument response. The recoveries are then compared. The recoveries can be determined as appropriate for each measurement procedure, and can be compared by calculating a ratio or difference, or otherwise.

Embodiments of this method can also include forming a reference quality control having a nominal analyte concentration different from that of the original quality control. Recoveries of the two or more procedures are also determined for the reference quality control and are termed reference recoveries. The reference recoveries can be compared with each other or with the recoveries determined from the original quality control. Using both quality controls, the sensitivities of the measurement procedures to the analyte of interest can be examined at multiple nominal concentrations of the analyte. Thus, systematic agreement or disagreement of the recoveries reported by multiple measurement procedures can be identified. To this end, if desired, additional reference quality controls can be prepared and recoveries can be determined at many nominal concentrations.

V. Examples

A. Expected Values Using Tables or Graphs Supplied by the Control Manufacturer

Figure 4:
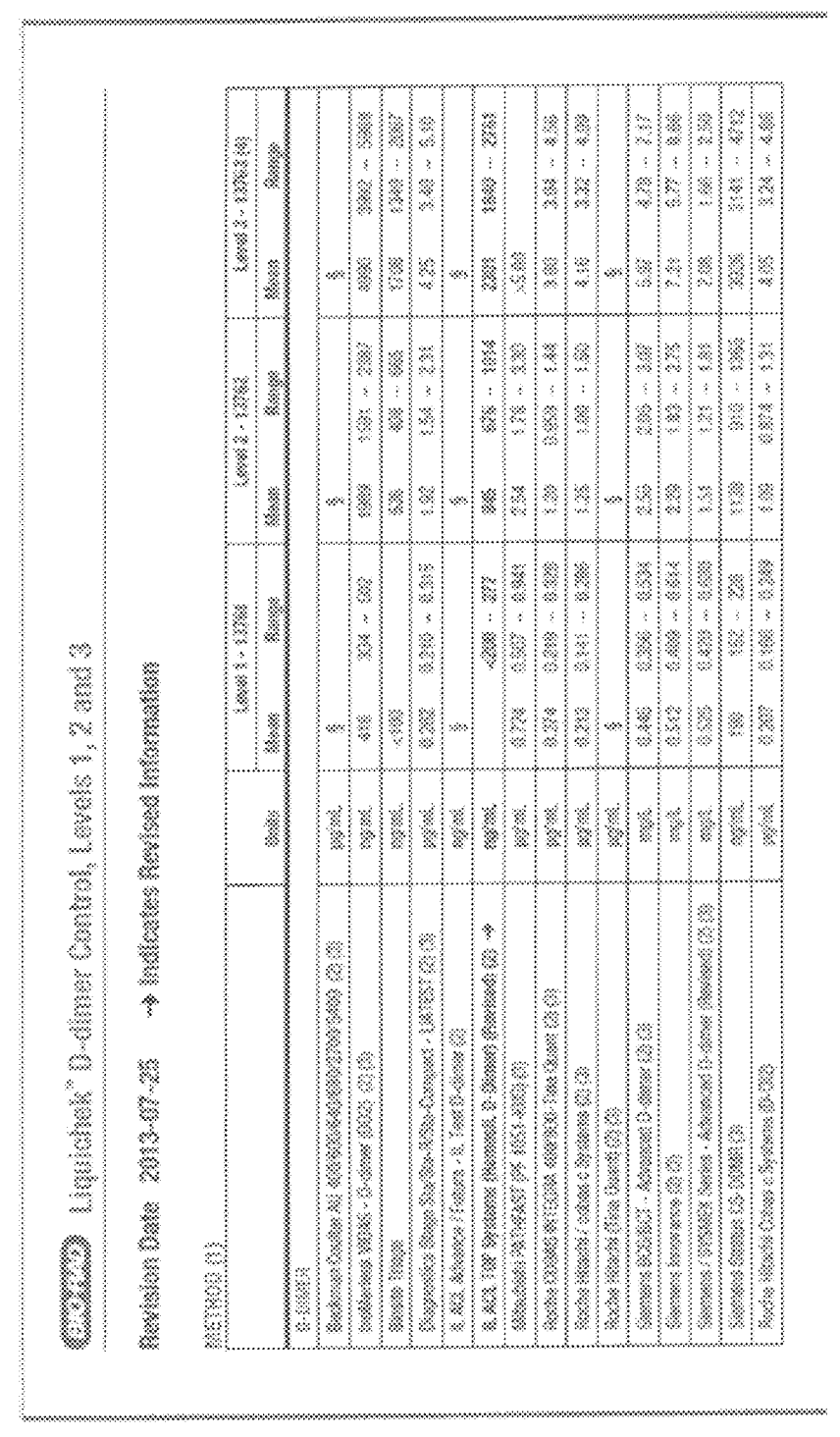

Presented in FIG. 4 is a typical value assignment table for three non-customizable quality controls. The quality controls, labeled "Level 1", "Level 2", and "Level 3", contain different nominal concentrations of the D-dimer analyte. Each row of the table provides an expected recovery, expressed as a mean and a range, of a particular measurement procedure for each quality control.

Figure 5:
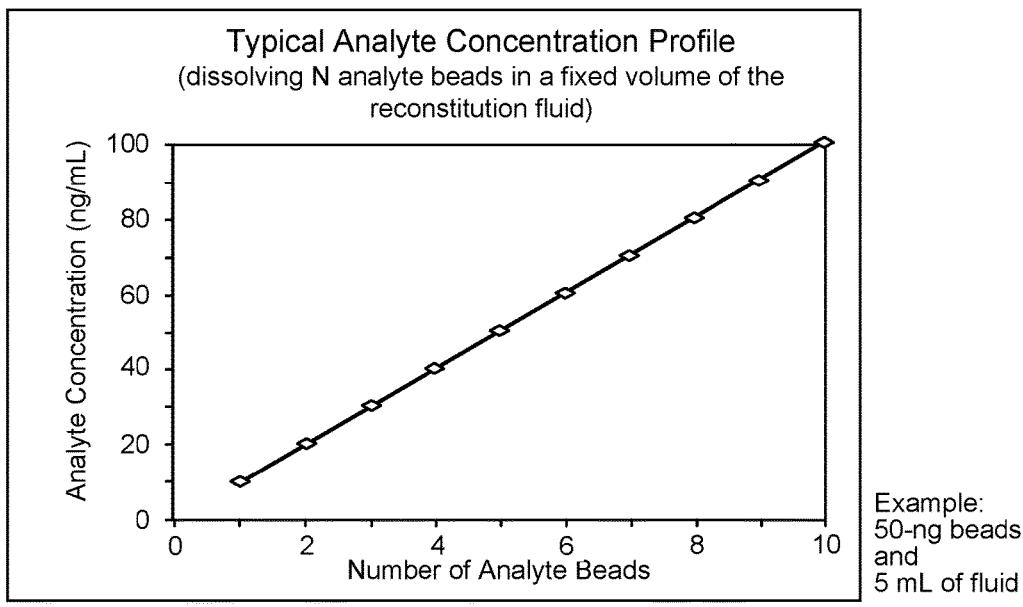
FIG. 5 shows a graph of analyte nominal concentration versus number of analyte beads for customizable quality controls.
Figure 6:
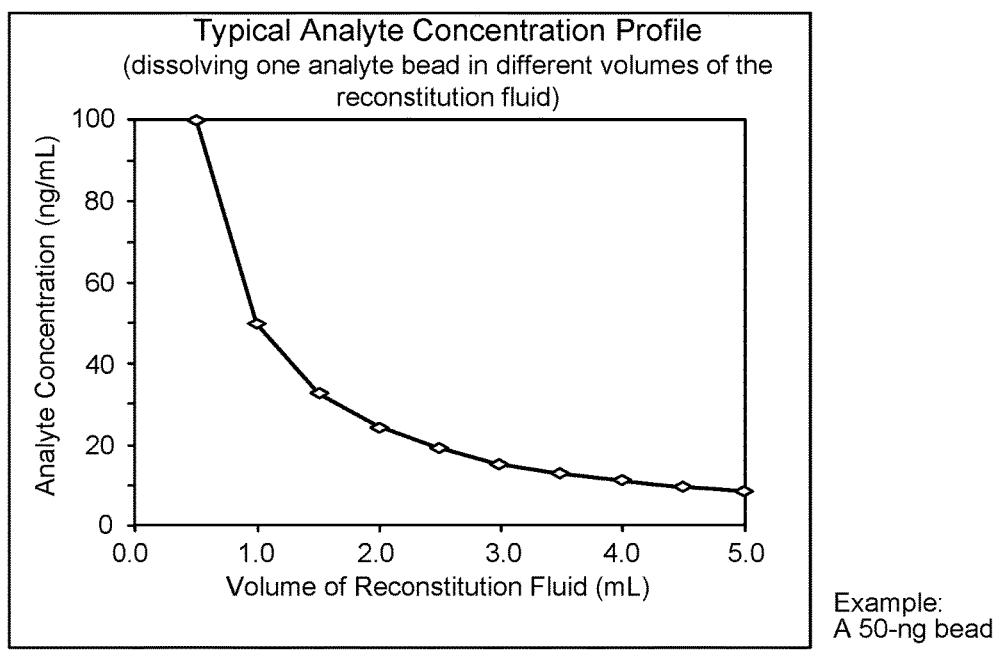
FIG. 6 shows a graph of analyte nominal concentration versus volume of base matrix for customizable quality controls.

Presented in FIGS. 5 and 6 are graphs that the end user of a diagnostic procedure can use to prepare customized quality controls having desired nominal concentrations of the analyte, when the amount of analyte per solid bead is known. FIG. 5 shows the nominal analyte concentrations in a series of customized quality controls prepared by dissolving different numbers of beads in a fixed volume of base matrix. The nominal concentrations have been determined empirically by the manufacturer of the beads and base matrix. The graph covers a broad range of nominal concentrations and preferably covers the reportable range of most measurement procedures. The end user can determine the expected nominal concentration in a particular quality control by reading a number from the graph or interpolating along the graph. For example, if nine beads each containing 50 ng of analyte are dissolved in 5 mL of base matrix, the nominal concentration of analyte in the resulting quality control is expected to be 90 ng/mL. FIG. 6 similarly shows the nominal analyte concentrations in another series of customized quality controls prepared by dissolving one 50 ng bead in different volumes of base matrix. If the bead is rehydrated in 3.5 mL of the base matrix, for example, the nominal concentration of analyte in the resulting quality control is expected to be 14 ng/mL. This nominal concentration can be read from the graph.

B. Example 2. Expected Recoveries Determined Using Spreadsheets

FIGS. 7 and 8 demonstrate an approach to estimating recoveries of various measurement procedures for T4 thyroid hormone.

Three reference customizable quality controls, containing low, medium, and high levels of T4 hormone, were prepared as described above. Each reference quality control was tested with seven different measurement procedures (Abbott Architect, Alfa Wasserman ACE, Beckman Coulter Unicel, Biomerieux Vidas, Ortho Vitros, Roche Elecsys, and Siemens Advia Centaur) and recoveries for each procedure were recorded. For each procedure besides Abbot Architect, the recoveries were plotted versus those obtained from the Abbott Architect procedure and linear regression was performed. The resulting linear fit function took a recovery from the Abbott Architect procedure at a given nominal T4 hormone concentration as the X value and returned a recovery for the other measurement procedure as the Y value. The fit function for each procedure had the form Recovery (procedure)=slope*Recovery (Abbott Architect)+intercept.

The fit functions for the different measurement procedures were used in the spreadsheet shown in FIGS. 7 and 8. This spreadsheet allows the end user to enter the number of solid beads and volume of base matrix used to prepare a new customizable quality control, and receive predicted recoveries of the seven measurement procedures as outputs. The recovery of the Abbott Architect procedure is determined by scaling the nominal concentration of T4 hormone in the quality control, which is expressed as the ratio of number of beads to volume of base matrix, by a correlation factor. The correlation factor is a scalar value based on historical data, and the scaling is done by multiplying the nominal concentration by the correlation factor. The recovery of each of the other measurement procedures is determined using the recovery of the Abbott Architect procedure and the appropriate fit function calculated above.

In FIG. 7, predicted recoveries of the seven measurement procedures are shown for a customizable quality control prepared by dissolving two beads in 5 mL of base matrix. In FIG. 8, expected recoveries of the seven procedures are shown for a customizable quality control prepared by dissolving two beads in 10 mL of base matrix.

Figure 9:
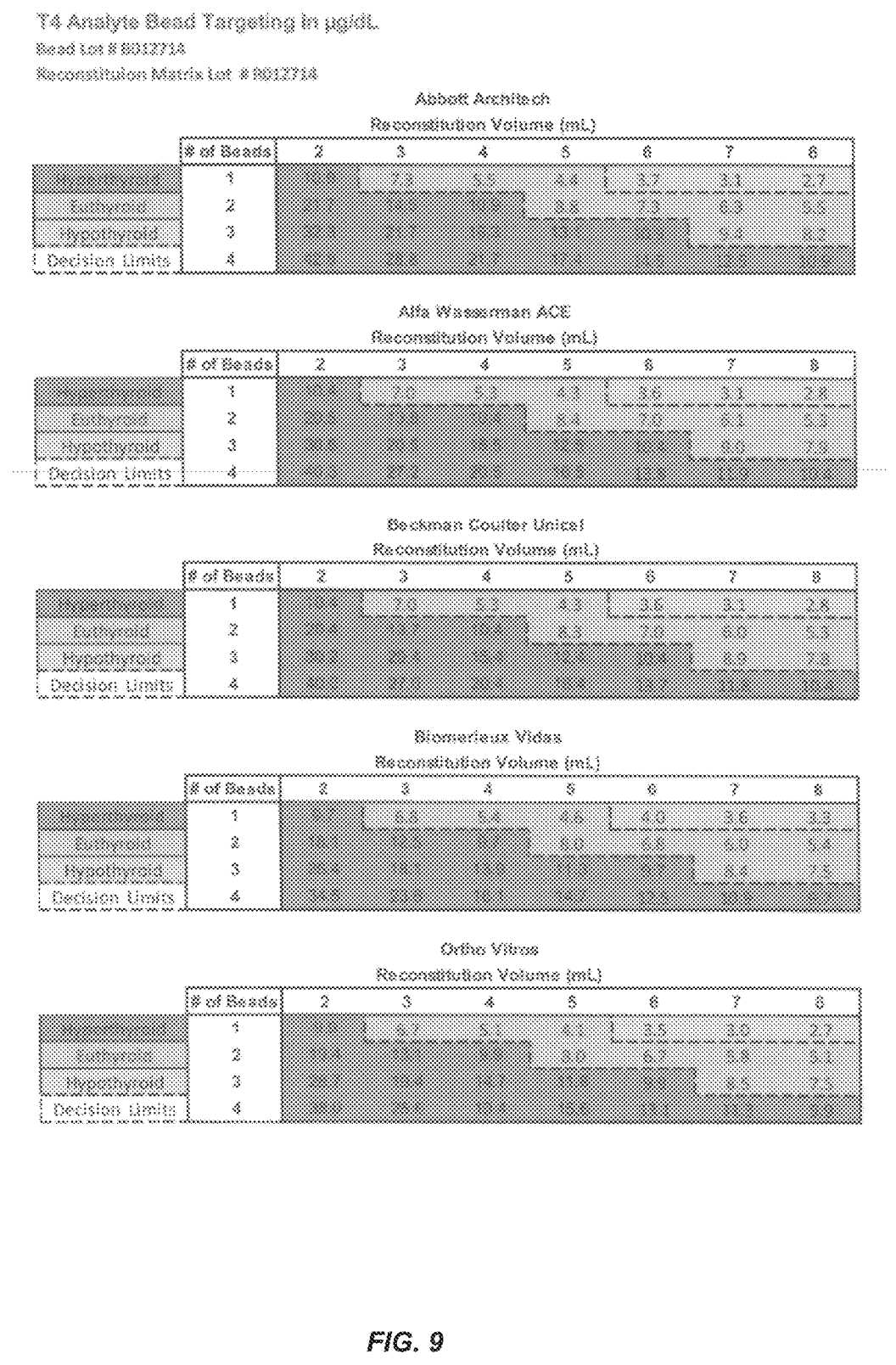

The T4 hormone recoveries that are output by the spreadsheet shown in FIGS. 7 and 8 can be tabulated as shown in FIG. 9. Each table in FIG. 9 shows the recoveries of one procedure calculated for various combinations of bead number and volume of base matrix. Each table also shows how the recoveries are positioned with respect to two medical decision points for distinguishing among hypothyroid, euthyroid, and hyperthyroid levels of T4 hormone. These medical decision points correspond to recoveries of approximately 4 and 10 µg/dL as measured using the Abbott Architect procedure.

C. Example 3. Value Assignment Example of Bead Based Control Using UNITY Data Customizable quality controls prepared from various numbers of T4 analyte beads and volumes of base matrix were measured on a Beckman Access instrument and recoveries were recorded (FIG. 10, top). The recoveries were then plotted versus the ratio of bead number to volume of base matrix (B/MV ratio). This ratio served as the nominal concentration of T4 hormone. Using least-squares regression (FIG. 10, middle), analyte recovery on the Beckman Access instrument was estimated as a function of this ratio using the equation Recovery=10.8*Ratio+0.0058. The function served as a correlation factor for scaling analyte nominal concentrations to obtain recoveries.

Next, using historical data from the Bio-Rad UNITY Interlaboratory Program for similar controls, recoveries of the Beckman Access instrument and other instruments were estimated at three levels of T4 hormone (FIG. 10, bottom). The recoveries of each other instrument were plotted against those of the Beckman Access instrument and a regression line was fitted to the data. The fit function converted the recovery of the Beckman Access instrument to that of the other instrument. For example, the recovery of the Beckman Access instrument was converted to the recovery of the TOSOH AIA instrument by the equation Recovery (TOSOH AIA)=0.91*Recovery (Beckman Access)+0.74.

Using the data in FIG. 7 taken together, and by combining the above equations, the recovery of any measurement procedure for T4 thyroid hormone can be estimated based on the number of beads and volume of base matrix in a customizable quality control. A spreadsheet can be provided to the end user to input the number of beads and volume of base matrix and predict recoveries on one or more instruments of choice.

VI. Computer Systems

Figure 11:
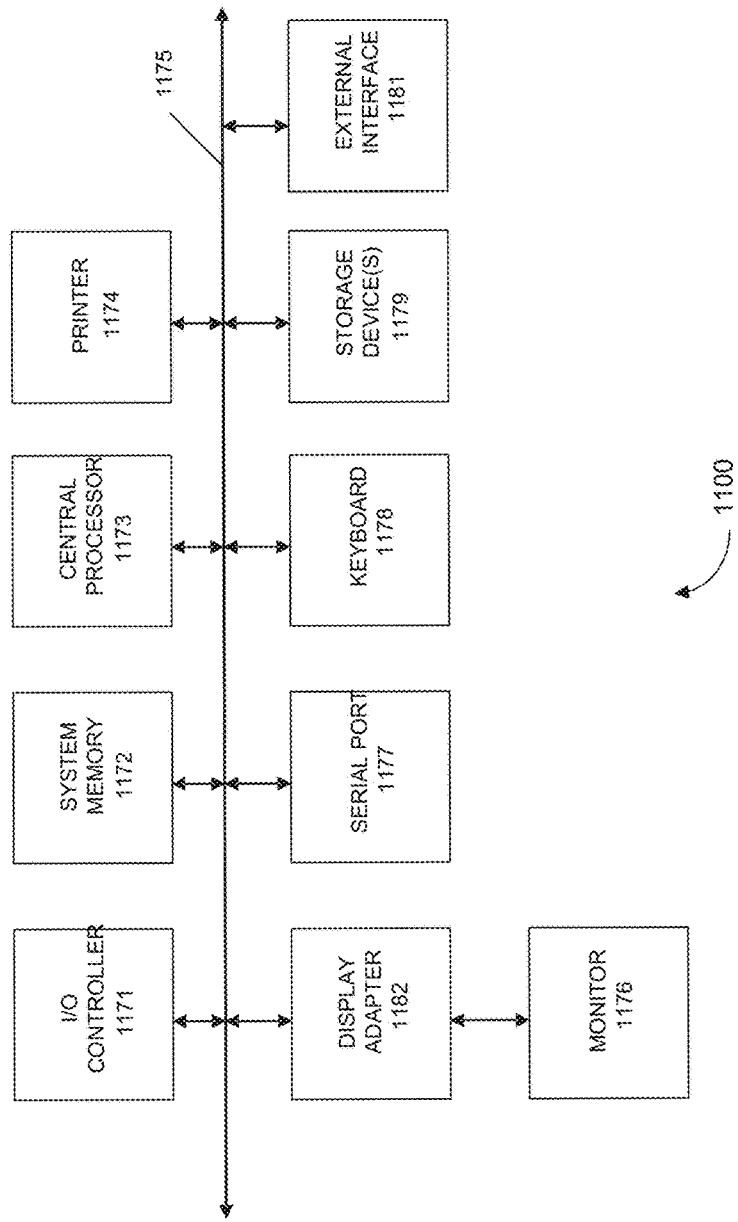
FIG. 11 shows a block diagram of a computer system 800 usable with embodiments of the present invention.

Any of the computer systems mentioned herein may utilize any suitable number of subsystems. Examples of such subsystems are shown in FIG. 11 in computer apparatus 1100. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 11 are interconnected via a system bus 1175. Additional subsystems such as a printer 1174, keyboard 1178, storage device(s) 1179, monitor 1176, which is coupled to display adapter 1182, and others are shown. Peripherals and input/output (I/O) devices, which couple to I/O controller 1171, can be connected to the computer system by any number of means known in the art, such as serial port 1177. For example, serial port 1177 or external interface 1181 (e.g. Ethernet, Wi-Fi, etc.) can be used to connect computer system 1100 to a wide area network such as the Internet, a mouse input device, or a scanner. The interconnection via system bus 1175 allows the central processor 1173 to communicate with each subsystem and to control the execution of instructions from system memory 1172 or the storage device(s) 1179 (e.g., a fixed disk, such as a hard drive or optical disk), as well as the exchange of information between subsystems. The system memory 1172 and/or the storage device(s) 1179 may embody a computer readable medium. Any of the data mentioned herein can be output from one component to another component and can be output to the user.

A computer system can include a plurality of the same components or subsystems, e.g., connected together by external interface 1181 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented procedures. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

\* \* \*

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of preparing a quality control for an analyte, the method comprising:
    applying a function to a desired reported concentration of an analyte in a quality control to return a target concentration of the analyte in the quality control, wherein the desired reported concentration is a concentration value desired to be obtained from a measurement procedure, wherein the measurement procedure is a technique or system for detecting a concentration of an analyte, and wherein the function is derived by applying regression analysis to analyte concentration data previously obtained using the measurement procedure;
    providing one or more solid beads containing the analyte, and a base matrix, wherein the solid beads are water-soluble spheres or pellets, and wherein the base matrix is a material substantially devoid of the analyte;
    determining a number of solid beads and a volume of the base matrix needed to prepare the quality control with the target concentration of the analyte; and
    dissolving the number of beads in the volume of the base matrix, thereby preparing the quality control for the analyte.

2. The method of claim 1, further comprising:
    designating one or more nearby reported analyte concentrations, wherein each nearby reported analyte concentration is at least 10% above or below the desired reported concentration of the analyte in the quality control; and
    estimating, using the function, concentrations of the analyte in one or more nearby quality controls corresponding to the one or more nearby reported analyte concentrations.

3. The method of claim 1, wherein the applying of the function returns a reference reported concentration of the analyte in the quality control, wherein the reference reported concentration is a concentration value obtained from a reference measurement procedure for the analyte, and wherein the function is derived by applying regression analysis to analyte concentration data previously obtained using the measurement procedure and the reference measurement procedure.

4. The method of claim 3, further comprising:
    designating one or more nearby reference reported analyte concentrations, wherein each nearby reference reported concentration of the analyte in the quality control is at least 10% above or below the reference reported concentration of the analyte in the quality control; and
    estimating, using the function, concentrations of the analyte in one or more quality controls corresponding to the nearby reference reported analyte concentrations.

5. The method of claim 1, wherein the applying of regression analysis comprises fitting a regression line to a plot of analyte concentration data previously obtained using the measurement procedure versus previous analyte concentrations.

6. A method of evaluating a predicted reported concentration of an analyte in a quality control as reported by a measurement procedure for the analyte, the method comprising:
    preparing a quality control having a concentration of the analyte;
    applying a function to the concentration of the analyte in the quality control to return a predicted reported concentration of the analyte in the quality control as reported by a measurement procedure, wherein the measurement procedure is a technique or system for detecting the concentration of the analyte, and wherein the function is derived by applying regression analysis to analyte concentration data previously obtained using the measurement procedure;
    testing the quality control using the measurement procedure, thereby obtaining a measurement response;
    determining an actual reported concentration of the measurement procedure for the analyte based on the measurement response;
    comparing the predicted reported concentration with the actual reported concentration, thereby evaluating the predicted reported concentration of the analyte in the quality control as reported by the measurement procedure for the analyte.

7. The method of claim 6, wherein preparing the quality control comprises adding a number of solid beads containing the analyte to a volume of a base matrix, wherein the solid beads are water soluble spheres or pellets, wherein the base matrix is a material substantially devoid of the analyte, and wherein the concentration of the analyte in the quality control is determined based on the number of beads and the volume of the base matrix.

8. The method of any one of claims 1-4 and 7, wherein the base matrix is obtained from one or more patient samples.

9. The method of claim 6, further comprising designating one or more nearby concentrations of the analyte, wherein each nearby concentration is at least 10% above or below the concentration of the analyte in the quality control; and
    obtaining, using the function, one or more predicted reported concentrations of the analyte corresponding to the one or more nearby concentrations of the analyte.

10. The method of claim 6, further comprising:
    obtaining a range of reported concentrations of the analyte as reported by the measurement procedure for the analyte, wherein the range contains the predicted reported concentration of the analyte.

11. The method of claim 6, wherein the applying of the function converts a reference reported concentration to the predicted reported concentration of the analyte in the quality control as reported by the measurement procedure, wherein the reference reported concentration is a concentration value obtained from a reference measurement procedure for the analyte at the concentration of the analyte in the quality control, and wherein the function is derived by applying regression analysis to analyte concentration data previously obtained using the measurement procedure and the reference measurement procedure.

12. The method of claim 6, wherein the applying of regression analysis comprises fitting a regression line to a plot of analyte concentration data previously obtained using the measurement procedure versus previous analyte concentrations.

\* \* \* \* \*